United States Patent [19]

Schmitt et al.

[11] Patent Number: 4,795,823
[45] Date of Patent: Jan. 3, 1989

[54] (METH)ACRYLIC ACID ESTERS AND THE USE THEREOF FOR PREPARING DENTAL COMPOSITIONS

[75] Inventors: Werner Schmitt, Starnberg; Peter Jochum, Seefeld; Wolf-Dietrich Zahler, Seefeld-Hechendorf; Heijo Hübner, Wörthsee/Steinebach; Manfred Holupirek, Grafrath; Oswald Gasser, Seefeld; Christian Herzig, Burghausen, all of Fed. Rep. of Germany

[73] Assignee: ESPE Stiftung & Co. Produktions, Seefeld, Fed. Rep. of Germany

[21] Appl. No.: 20,902

[22] Filed: Mar. 2, 1987

[30] Foreign Application Priority Data

Mar. 6, 1986 [DE] Fed. Rep. of Germany ....... 3607331

[51] Int. Cl.$^4$ ............................................. C07C 69/66
[52] U.S. Cl. .................................. 560/182; 522/179; 522/908; 523/120; 526/323; 526/322
[58] Field of Search ................ 560/182; 522/179, 908; 523/120; 526/322; 520/323

[56] References Cited

U.S. PATENT DOCUMENTS

| 2,608,578 | 8/1952 | Weesner | 560/182 |
| 2,815,354 | 12/1957 | Wilkinson | 560/182 |
| 3,527,737 | 9/1970 | Masuhara | 560/182 |

Primary Examiner—Paul J. Killos
Attorney, Agent, or Firm—Birch, Stewart, Kolasch & Birch

[57] ABSTRACT (Methy)acrylic acid esters of the general formula

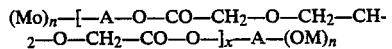

$$(Mo)_n-[-A-O-CO-CH_2-O-CH_2-CH_2-O-CH_2-CO-O-]_x-A-(OM)_n$$

are described wherein

A is an alcohol radical having at least 4 chain atoms between two junction sites.

M is $CH_2=C(R^1)-CO$ wherein $R^1$ stands for hydrogen or methyl, n is 1 or 2, and x is 0.3 to 3.

These esters are suited for the preparation of dental compositions.

14 Claims, No Drawings

(METH)ACRYLIC ACID ESTERS AND THE USE THEREOF FOR PREPARING DENTAL COMPOSITIONS

FIELD OF THE INVENTION

The invention relates to new (meth)acrylic acid esters and the use thereof for the preparation of dental compositions.

BACKGROUND OF THE INVENTION

Synthetic resin materials, especially polymers of readily polymerizable, olefinically unsaturated compounds; in addition to material such as amalgam, gold and porcelain, are used for making tooth fillings, tooth sealings and facings for crowns, bridges and for replacing teeth. Synthetic resins offer the advantage of being acceptable from a cosmetic point of view relative to the other materials and are impact resistant, unlike porcelain, for example.

About 45 years ago poly(methyl methacrylate) was used for the first time for the above-identified purposes. However, the preparation of tooth fillings required that the polymerization can be carried out only at normal or body temperature. As a result, however, a small portion of the methyl methacrylate invariably remains unpolymerized in most cases causing death of the pulp because it has been proven that residual monomers gradually diffuse out of the filling resulting in such damage.

During the past few decades the dental industry has substituted these polymers with polyfunctional methacrylic acid esters such as bisglycidyl methacrylates of isopropylidene phenol which are described in U.S. Pat. No. 3,066,122 and are known by the name of bis-GMA. Several disadvantages of these monomers including high viscosity and swelling in water could be overcome by a modification thereof with isocyanates (U.S. Pat. No. 3,629,187) or by the use of other diphenols or alkanediols. Examples for such monomers are given in German Patent Nos. 1,921,869, 2,816,823 and 2,934,380 or U.S. Pat. Nos. 3,629,187 and 4,406,625.

In addition, German Inspection Specification 25 41 641 discloses that radiation-hardening binders on the basis of unsaturated polyesters are known and are to be used preferably in solvent-free printing inks.

However, all the hitherto described monomers are subject to substantial shrinkage upon polymerization so that large quantities of inorganic filler must be added in order to control the shrinkage within acceptable limits. Nevertheless, the existing polymerization shrinkage still regularly results in a marginal gap between the tooth and the synthetic resin filling, or between the metal and the synthetic resin facing which results in poor adhesion and which allows bacteria to enter the gap thereby initiating secondary caries.

The use of the etch-and-bond technique or the use of so-called dentine adhesives allows the polymerization shrinkage to be displaced from the margin of the filling into the filling itself, so that despite a certain polymerization shrinkage the adhesion between the tooth and the synthetic resin filling or between the metal and the synthetic resin facing is warranted. However, this requires a highly sophisticated processing technique. Thus, processing defects can be avoided only by utmost care and become apparent only after 1 to 2 years much to the patient's regret.

SUMMARY OF THE INVENTION

Accordingly, it is an object of the present invention to provide novel (meth)acrylic acid esters which are suited for the preparation of low-shrinkage dental compositions.

According to the invention, this object is realized by the provision of (meth)acrylates of the general formula:

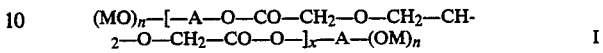

$$(MO)_n-[-A-O-CO-CH_2-O-CH_2-CH_2-O-CH_2-CO-O-]_x-A-(OM)_n \quad I$$

wherein
A is an alcohol radical with at least 4 chain atoms between two junction sites,
M is $CH_2=C(R^1)-CO-$, wherein $R^1$ stands for hydrogen or methyl,
n is 1 or 2,
x is 0.3 to 3.
Preferably x is 0.5 to 2.

The dental compositions obtained by the use of the novel (meth)acrylic acid esters of the present invention exhibit a markedly lower polymerization shrinkage than dental compositions prepared with known bifunctional or polyfunctional monomers.

DETAILED DESCRIPTION OF THE INVENTION

The (meth)acrylates of Formula are described in more detail below.

The (meth)acrylic acid esters of the present invention are preferably used in the form of mixtures of compounds of Formula I, wherein x has various values between 1 and 3 and especially a mixture of two compounds wherein x=1 and 2 in a molar ratio of 1:1.

The radical A preferably has at least 8 chain atoms and not more than 30 chain atoms between two junction sites. The chain atoms may be C, 0, N, S and P. The chains between two junction sites may have pendant groups.

Suitable alcohols $A(OH)_{n+1}$ are, for example, alkanediols, cycloalkanediols, alkoxylated cycloalkanediols and bisphenol-A derivatives, especially alkoxylated bisphenol-A dervatives. Preferred alcohols are n-dodecyl-1,12-diol, the bis-(2-hydroxyethylether) and bis-(2-hydroxypropylethers) of 2,2-isopropylidene diphenol, especially bis-(hydroxymethyl)tricyclo-[5.2.1.0$^{2,6}$]-decane.

The alcohol $A(OH)_{n+1}$ is esterified, on the one hand, with triglycolic acid, and on the other hand with acrylic or methacrylic acid.

Examples of monomers suitable for the present invention include triglycolic acid-bis[3(4)-methacryloxymethyl-8(9)-tricyclo-[5.2.1.0$^{2,6}$]-decylmethyl ester], triglycolic acid-bis-[3(4)-acryloxymethyl-8(9)-tricyclo[5.2.1.0$^{2,6}$]-decylmethyl ester], triglycolicacid-bis-[octyloxymethacrylate], triglycolic acid-bis[dodecyloxymethacrylate], and triglycolic acid-bis-[4-methacryloxyethoxy-4-2,2-diphenylpropyl ester].

The compounds and mixtures of compounds according to the invention generally are moderately viscous liquids or relatively low melting substances. They are prepared in a manner known per se by conventional methods of esterification or ester interchange. Thus, for instance, the polyols can be esterified or partially esterified directly with triglycolic acid in the presence of known esterification catalysts, such as paratoluene sulfonic acid. The remaining hydroxyl functions of the polyol are esterified with the addition of customary polymerization inhibitors, e.g., picric acid, methylene blue and ionol, with methacrylic or acrylic acid.

The esters according to the invention can be easily polymerized by free radical forming agents in a manner conventional for (meth)acrylic acid esters.

Suitable initiator systems are, for example, known redox systems. By means of these initiators the esters according to the invention can be completely polymerized within a few minutes at room or body temperature. Systems that have no discoloration tendencies are preferred, e.g., the known sulfone derivates, such as hydroxysulfones or aminosulfones. Also soluble salts of sulfinic acids with tertiary amines or quaternary ammonium bases, especially in combination with peroxides, are suitable. So-called CH-active substances, such as β-diketone derivatives or barbituric acid derivatives monosubstituted in the 5-position can be used in combination with known cocatalysts such as heavy metal traces and chloride ions.

Further free radical formers are known, for example, from German Pat. No. 942,540, French Pat. No. 981,085, and German Opposition Specification Nos. 1,037,132, 1,065,617 and 1,217,063. The following compounds are suited, for example, as peroxides: benzoyl peroxide, lauroyl peroxide, mono-t-butyl permaleinate or t-butyl hydroperoxide. Among the azocarboxylic acid nitriles, azo-isobutyronitrile comes into consideration, inter alia.

Another particularly suited initiator system is a photoinitiator system. Photoinitiators are described, for example, in German Inspection Specification Nos. 2,251,048 and 2,003,132 and in U.S. Pat. Nos. 2,548,685, 2,495,987, 3,551,246 and 3,558,387 and in European Patent Publication No. 0 073 413. By way of example, benzoine ether, benzophenones and diketones, e.g., camphor quinone or benzile, are mentioned. The photoinitiators can be employed optionally together with activators. Suitable activators are, for example, amines, especially tertiary amines, as well as the activators (reducing agents) mentioned, for example, in German Inspection Specification 2,251,048. In general, the photoinitiator is formulated in an amount of 0.01 to 10% by weight based on the polymerizable monomer mixture.

The compounds or mixtures of compounds according to the invention can be employed per se or together with other polymerizable ethylenically unsaturated monomers for the preparation of dental compositions. In the individual case this can be reasonable in order to attain the desired viscosity of the monomer mixture. Monomers of the invention corresponding to Formula I having chain lengths of x>1 and alcohol radicals A with more than 8 chain atoms may be reasonably used along with low-viscosity monomers.

Suitable low viscosity monomers are, for example, the acrylic acid esters and methacrylic acid esters of mono- or polyfunctional alcohols. Such alcohols are represented, for example, by the general formula $A(OH)_{n+1}$. In addition, acrylic acid esters and methacrylic acid esters of mono- or polyfunctional alcohols with chain members less than 4 are suitable, e.g. methanol, ethanol and ethylene glycol. Preferably, the alcohol moiety of the low-viscosity monomers is equal to that used in the selected compounds according to the invention. Most preferred low viscosity monomers are the acrylic acid esters and methacrylic acid esters of bis-(hydroxymethyl)-tricyclo[5.2.1.0$^{2,6}$]-decane.

The dental composition prepared from the (meth)acrylic acid esters of the invention must also contain the above mentioned initiator, e.g. a peroxide, such as benzoyl peroxide, and optionally an activator, e.g. a tertiary amine, such as N,N-dimethyl-p-toluidine when polymerizing and curing occurs on the tooth surface or in a tooth cavity. Such a curing system is added in an amount of 0.1 to 6% by weight based on the polymerizable monomer mixture. To this end, the polymerizable dental composition contains at least two separate packages, one of which containing the initiator and the other one containing the activator. Before the dental composition is used, the contents of the two packages are blended or mixed. When denture parts are made with lauroyl peroxide, the composition is suitably heated in a mold for several hours to 90° C. or for a short time to temperatures up to about 160° C., preferably to 120° to 60° C.

Fillers are suitably added in the preparation of the instant dental compositions at a concentration of 20 to 95%, preferably 40 to 85%, to the monomers of the invention. Suitable filler materials are, for example, finely particulate polymethyl methacrylate, glass or quartz fibers, quartz powder, alumina silicates, pyrogenic silica, silica gels, or agglomerates or granules prepared from the last two products. Furthermore, the addition of pigments is advantageous in order to obtain a tooth-like coloration of the polymerizable dental material.

It may be further advantageous to add to the dental composition x-ray-opaque additives, such as barium sulfate, zirconia, or barium and strontium glass. These substances may be added to the filler at a concentration of 1 to 100% based on the filler content.

The use of fillers pre-treated with a coupling agent is particularly advantageous. Suitable coupling agents include silanes, for example, trimethoxy-methacrylpropoxysilane.

The dental compositions obtained by the use of the esters according to the invention surprisingly exhibit a markedly lower polymerization shrinkage than dental compositions prepared with known bifunctional or polyfunctional monomers. The use of esters according to the invention is especially advantageous in dental compositions into which only small amounts of inorganic filler can be introduced, such as in dental compositions prepared with so-called microfillers. Normally, such compositions contain less than 70% by weight of inorganic filler. In contrast to the so-called "macrofilled dental compositions", the "microfilled dental compositions" can be polished so that they allow the production of "cosmetically perfect" tooth fillings and facings. The dental compositions prepared with known monomers exhibit marked polymerization shrinkage after curing.

Accordingly, dental compositions prepared from monomers according to the invention allow the use of less filler while maintaining the same favorable shrinkage properties that can be conventionally obtained only with very highly filled compositions.

EXAMPLE 1 (PREPARATION EXAMPLE)

Triglycolic acid-bis[3(4)-methacryloxymethyl-8(9)-tricyclo[5.2.1.0$^{2,6}$]-decylmethylester]

196 Grams (1.0 mol) of bis-(hydroxymethyl)-tricyclo[5.2.1.0$^{2,6}$]-decane (T-diol) is dissolved in 400 ml cyclohexane and is partially esterified with an extraction of 18 g water and with 89 g (0.5 mol) triglycolic acid. 7 Grams p-toluenesulfonic acid is used as a catalyst. The remaining hydroxyl functions of the diol are esterified by the addition of 80 mg picric acid, 200 mg methylene blue, and 35 mg ionol as polymerization inhibitors and with 129 g (1.5 mol) of freshly distilled methacrylic acid whereupon an additional 18 grams of water separate. The crude ester mixture is diluted with an additional 400 ml cyclohexane and 250 ml toluene and is washed with 4×350 ml 2N NaOH, 2×350 ml 0.5N $H_2SO_4$, and with water. The ester solution is dried with sodium sulfate, atmospheric oxygen is bubbled therethrough, and then the solution is purified over alumina. After the addition of 4-methoxyphenol for inhibition, 258 g of an ester mixture having the following average composition is obtained by concentration under a high vacuum:

32% T-diol-bis-methacrylate
38% triglycolic acid-bis[T-methacrylate]
30% bis(methacrylate) of

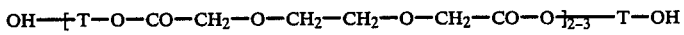

$$OH-[-T-O-CO-CH_2-O-CH_2-CH_2-O-CH_2-CO-O-]_{2-3}-T-OH$$

viscosity: 80 poises
density: 1.152 g/ml
$n_p^{20}$: 1.496
'H-NMR: 0 9-2.7 ppm (Tricyclus), 1.97 ppm ($CH_3-C=C$), 3.77 ppm ($O-CH_2-CH_2-O$), 3.7-4.2 ppm (tricyclo-$CH_2-O$), 4.17 ppm ($O-CH_2-CO_2-$), 5.54 ppm (trans-$CH=C-C=O$), 6.09 ppm (Cis-$CH=C-O$).
IR (Film): $\nu(C-H)=2940, 2870$ cm$^{-1}$,
$\nu(C=O)=1751, 1715$ cm$^{-1}$,
$\nu(C=C)=1635$ cm$^{-1}$,
$\nu(C-O)=1196, 1160, 1130$ cm$^{-1}$.

EXAMPLE 2 (USE EXAMPLE)

50 parts by weight of bis-(acryloxymethyl)-tricyclo[5.2.1.0$^{2,6}$]decane and 50 parts by weight of the ester mixture obtained in Example 1 are stirred with careful heating until a clear solution has formed.

0.15% by weight of camphor quinone is added along with 1.5% by weight of N,N-dimethylaminoethyl methacrylate to the solution which has cooled to room temperature and the mixture is stirred until a clear solution is obtained.

112 Parts by weight of silanized silica granules (European Patent 0 040 232), 72 parts by weight of silanized pyrogenic silica (Aerosil OX 50 manufactured by Degussa) and 3 g calcium fluoride are blended to form a homogeneous powder and colored similar to natural teeth.

113 g of this powder is added in small portions to 80 g of the solution and is masticated to a tooth filling composition having an uniform pasty consistency.

When the resulting tooth filling composition is filled into a cylinder (5 mm diameter, 8 mm length) and exposed for 20 seconds to a commerically available dental irradiating device (Elipar-Visio/ESPE), then the polymer is removed from the cylinder and the soft or gel-like incompletely polymerized components are scraped off with a plastic spatula thereby producing a completely polymerized layer having a thickness of 3.4 mm. The resistance to pressure is 431.5N/mm$^2$.

EXAMPLE 3 (USE EXAMPLE)

Cylindrical cavities having a diameter of 3 mm are labially cut into the tooth enamel of extracted bovine incisors. The cut cavities have a depth of 2.5 mm.

The dental filling compositions to be tested are introduced into the cavities and cured for 20 seconds with a commerical dental irradiating device (Elipar-Visio/ESPE).

The tooth filling composition described in Example 2 is used along with a composition having the same filler composition but with a monomer mixture customary for tooth filling compositions e.g containing 45 parts of bis(acryloxymethyl)-tricyclo[5.2.1.0$^{2,6}$]-decane, 45 parts of bis-(methacryloxymethyl)tricyclo[5.2.1.0$^{2,6}$]-decane and b 10 parts of bis-GMA.

The marginal gap formation is microscopically measured by means of a section through the bovine tooth in a direction at right angles to the filling surface at the bottom, in the middle, and at the upper margin on each of 5 teeth. The following table lists the average values of the measurements.

TABLE

| Tooth Filling Composition | Polymerization Shrinkage ($\mu$m) | | |
|---|---|---|---|
| | Middle | Bottom | Upper Rim |
| According to Example 2 | 3 ± 2.3 | 7.0 ± 2.3 | 2 ± 1.1 |
| Comparative Preparation | 12.3 ± 5.3 | 21.0 ± 9.1 | 4.8 ± 5.6 |

The results indicate that the polymerization shrinkage of the tooth composition for the monomer mixture according to the invention is lower by a factor of 2 to 3 relative to the comparative preparation which is filled with the same filler.

Further scope of applicability of the present invention may be apparent from the detailed description given hereinabove. However, it should be understood that the detailed description and specific examples, while indicating preferred embodiments of the invention, are given by way of illustration only, since various changes and modifications within the spirit and scope of the invention may be apparent to those skilled in the art from this detailed description.

We claim:
1. (Meth)acrylic acid esters of the formula:

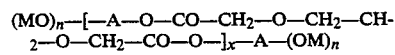

$$(MO)_n-[-A-O-CO-CH_2-O-CH_2-CH_2-O-CH_2-CO-O-]_x-A-(OM)_n$$

wherein,
A is an alcohol radical having at least 4 chain atoms between two junction sites,
M represents $CH_2=C(R^1)-CO-$, wherein $R^1$ is hydrogen or methyl,
n is 1 or 2, and
x is 0.3 to 3.
2. The compound according to claim 1, wherein n is 1.
3. The compound according to claim 2, wherein x is 0.5 to 2.
4. The compound according to claim 1, wherein A has at least 8 chain atoms.
5. The compound according to claim 1, wherein A is an alcohol radical selected from the group consisting of n-dodecyl-1,12-diol, bis-(2 hydroxyethyl ether) and bis-(2-hydroxypropyl ether) of 2,2 isopropylidene diphenol, and bis-(hydroxymethyl)tricyclo[5.2.1.0$^{2,6}$]decane.

6. The compound according to claim 3, wherein A is an alcohol radical selected from the group consisting of n-dodecyl-1,12-diol, bis-(2 hydroxyethyl ether) and bis-(2-hydroxypropyl)ether) of 2,2-iscpropylidene diphenol, and bis-(hydroxymethyl)-tricyclo[5.2.1.0$^{2,6}$]-decane.

7. A dental composition comprising the compound according to claim 1 and an effective amount of an initiator system for polymerizing said (meth)acrylic acid esters at room or body temperature.

8. A dental composition comprising a mixture of two compounds according to claim 1 in a molar ratio of 1:1, wherein in one compound x=1 and in the other compound x=2 and an effective amount of an initiator system for polymerizing said (meth)acrylic acid esters at room temperature.

9. The dental composition according to claim 7 further comprising polymerizable ethylenically unsaturated monomers.

10. The dental composition according to claim 7 further comprising esters of (meth)acrylic acid and monofunctional or polyfunctional alcohol.

11. The dental composition according to claim 10, wherein the monofunctional or polyfunctional alcohols have the formula A(OH)$_{n+1}$.

12. The dental composition according to claim 10, wherein the monofunctional or polyfunctional alcohols are selected from the group consisting of alkanediols, cycloalkanediols, alkoxylated cycloalkanediols, bisphenol-A derivatives, alkoxylated bisphenol-A derivatives, n-dodecyl-1,12-diol, bis-(2-hydroxyethylether) and bis-(2-hydroxypropylether)of 2,2-isopropylidene diphenol, and bis-(hydroxymethyl)trioyclo-[5.2.1.0$^{2,6}$]-decane.

13. The dental composition according to claim 7, further comprising an effective amount of fillers, or pigments, or x-ray-opaque additives.

14. The dental composition according to claim 7, wherein the initiator system is a photoinitiator system.

* * * * *

UNITED STATES PATENT AND TRADEMARK OFFICE
CERTIFICATE OF CORRECTION

PATENT NO. : 4,795,823

DATED : January 3, 1989

INVENTOR(S) : SCHMITT et al

It is certified that error appears in the above-identified patent and that said Letters Patent is hereby corrected as shown below:

ON THE TITLE PAGE:

The name of the Assignee should be changed from "ESPE Stiftung & Co. Produktions" to --ESPE Stiftung & Co. Produktions- und Vertriebs KG--

The formula in the Abstract of the Disclosure, at line 2, should be changed from "$(Mo)_n$" to --$(MO)_n$--

Signed and Sealed this

Tenth Day of October, 1989

Attest:

DONALD J. QUIGG

Attesting Officer

Commissioner of Patents and Trademarks